United States Patent [19]

Prandi

[11] 4,387,031

[45] Jun. 7, 1983

[54] COMPOSITIONS ABLE TO SEPARATE THE ERYTHROCYTES FROM THE SERUM OR PLASMA IN BLOOD ANALYSIS SAMPLES, AND THE METHOD WHICH USES THEM

[76] Inventor: Luigi Prandi, Piazza Sordello, 43, 46100 Mantova, Italy

[21] Appl. No.: 285,019

[22] Filed: Jul. 20, 1981

[30] Foreign Application Priority Data

Jul. 22, 1980 [IT] Italy .............................. 23609 A/80

[51] Int. Cl.$^3$ ............................................ B01D 23/00
[52] U.S. Cl. .................................... 210/787; 524/481; 525/104; 525/100; 525/105; 525/431
[58] Field of Search ............... 525/104, 100, 105, 431; 524/481; 210/787

[56] References Cited

U.S. PATENT DOCUMENTS

| 2,792,309 | 5/1957 | Teichmann | 525/100 |
| 3,385,812 | 5/1968 | Brachman | 525/104 |
| 3,526,522 | 9/1970 | Seregely | 524/481 |
| 3,969,308 | 7/1976 | Penneck | 525/105 |

FOREIGN PATENT DOCUMENTS 565863 11/1958 Canada ............................. 525/105

Primary Examiner—Joseph L. Schofer
Assistant Examiner—N. Sarofim
Attorney, Agent, or Firm—Stevens, Davis, Miller & Mosher

[57] ABSTRACT

Compositions based on polydimethylsiloxane and physiologically inert powdered polymers, which are able to create a sharp separation layer between the erythrocytes and the serum or plasma during the centrifuging of blood samples for medical analyses.

5 Claims, No Drawings

COMPOSITIONS ABLE TO SEPARATE THE ERYTHROCYTES FROM THE SERUM OR PLASMA IN BLOOD ANALYSIS SAMPLES, AND THE METHOD WHICH USES THEM

This invention relates to new compositions able to constitute a highly effective separation layer between the layer of erythrocytes which precipitates and possibly coagulates during blood centrifuging, and the layer of plasma or serum which floats on it.

The invention also relates to a highly effective method of separating the erythrocytes from the plasma or blood by centrifuging, using the new mixtures according to the invention as the separation medium.

It is well known that although in recent years many automatic and semi-automatic devices have been designed for accelerating the chemical analysis of the blood, the initial preparation of the samples is always carried out in the same manner by pouring the withdrawn blood into a suitable sample tube, centrifuging the sample and decanting the supernatant layer of serum or plasma.

However, during this first decantation it is impossible to completely separate the erythrocytes from the supernanant, so that it is necessary to subject it to further centrifuging and again collect the serum or plasma for analysis.

Such a method is very long, in that the centrifuging stage is slow, and the pouring operations, which are carried out manually, must be effected carefully and slowly in order to prevent spillage of the samples and consequent contamination thereof or contamination of the operator. Moreover, double centrifuging necessarily implies a considerable loss of analysis material. This is also a considerable drawback in that under certain technical conditions such as small-quantity withdrawals or withdrawals from children it is necessary to obtain the maximum possible quantity of serum or plasma uncontaminated by erythrocytes for analysis. Thus, in general, because of the large number of blood analysis tests required at the present time, it is always necessary to obtain the maximum possible quantity of serum or plasma from a blood sample, in order to avoid having to make large-quantity withdrawals.

It has now been found, and forms the subject matter of the present invention, that it is possible to preload into the centrifuging sample tube, or to add to it when required, a mixture of substances able to form a sharp separation layer between the erythrocytes and the serum or plasma, so allowing separation of the supernanant to be analysed in a single centrifuging and decanting operation, and thus with a considerable saving of time and material.

In addition, the new mixture present in the blood sample during centrifuging exerts a certain filtration action on it by entraining the macromolecular fragments and possible particles present therein. Clear samples are thus obtained, which enable the analyses to be carried out under the best standard conditions.

In reality, the known art already possesses separation-filtration devices for blood analysis samples, but none of these has really constituted a solution to the problem. Firstly, in all cases the cost of the device represents a considerable proportion of total costs, and the time necessary for the further manual operation of inserting the device into the sample tube increases the total time, the length and delicacy of this operation varying with the type of device. Secondly, in addition to giving imperfect results because of the difficulty in exactly controlling their density, all the separating fluids used up to the present time inside the devices have shown a tendency to leave fragments or droplets in the serum or plasma, which tend to clog the analysis instruments.

The new blood separation-filtration compositions according to the present invention are constituted essentially by the following components:
  a'a polydimethylsiloxane having a viscosity of between 5000 cst and 60,000 cst, and a density of between 0.965 and 0.980 g/cm$^3$
  b—a chemically and physiologically inert macromolecular substance ground to a particle size of between 0.200 and 450$\mu$, and having a specific gravity of between 1.30 and 1.80, and chosen from the group consisting of polyolefine resins, polyvinyl resins, fluorinated polyolefines and polyester resins.

The component (a) constitutes the basis of the separating layer, while the macromolecular substance serves to adjust the density of the mixture to the required value in order to give it a consistency which can vary within a wide range according to the method used for its introduction into the sample tube. In addition, the resin gives the mixture its filtration power.

The choice of molecular weight of the silicone oil and of the polymer particle size is also determined by the mutual compatibility, in that there must be no absorption of oil in the resin.

The particle size of the polymer also influences the uniformity of the product, so that smaller particle sizes give more uniform pastes.

In addition to these basic components, the mixtures can also comprise components which are non-essential but sometimes useful, namely:
  c—a fluid polyisobutylene having a viscosity of between 0.30 and 250 poises and a density of between 0.833 and 0.889 g/cm$^3$
  d—amorphous micronised silica having a primary particle size of between 5 and 3 nm, an apparent density of about 30–80 g/l and a specific gravity of 2.15.

It has been found that the polyisobutylene can partly replace the silicone oil. The separation and filtration power of the mixture is reduced slightly, but there is a considerable saving from the economical viewpoint.

The micronised silica has the specific effect of conferring thixotropic properties on those compositions which do not possess them, or of improving them in those compositions which already possess them.

However, it has been found that beyond a certain limit the thixotropic agent does not further increase the thixotropic properties of the mixture, but instead causes a slight mixture densification.

The micronised silica also influences the uniformity of the mixtures.

In the case of mixtures based on fluorinated polymers, the use of the silica enables a polydimethylsiloxane of lower molecular weight to be used, for equal polymers used.

The new mixtures according to the invention must in all cases have a specific gravity of between 1.010 and 1.100, and a consistency varying from fluid wax to solid paraffin.

They can be used by preloading them into the analysis sample tubes before they are made up, possibly together with small quantities of anticoagulant. In such a case the mixtures must be of compact consistency and of considerable thixotropic power. Alternatively, the mixtures can be added to the sample tubes at the time of analysis, and in such a case it is preferable for them to be of more fluid consistency. It is also possible to use particularly compact mixtures for sealing the sample tubes containing the blood to be analysed, and for preserving them in a reliable manner free from any risk of contamination until the time for their analysis.

On centrifuging, the mixture becomes fluid and slides into the sample tube to form the separation layer.

The quantity of mixture necessary for each analysis varies according to its particular nature. However, only very small quantities of between 0.5 and 2 grams are necessary.

The separation-filtration mixture acts after 6–8 minutes of centrifuging.

Some non-limiting illustrative examples are given hereinafter in order to clarify the contents of the present invention.

EXAMPLE 1

Binary composition with polyolefine resin

| | |
|---|---|
| silicon oil of 5000 cst density 0.97 g/cm$^3$ | 74.5 parts by weight |
| polyethylene filled with TiO$_2$ ground to a particle size of $\leq 400\mu$, specific gravity 1.38 | 25.5 parts by weight |

These are mixed in a mixer for some minutes.

A consistent white paste having a specific gravity of 1.045 and thixotropic properties is obtained, which can be used equally well either by preloading into the sample analysis tubes or by adding when required.

It has excellent separation and filtration power and gives a clear serum or plasma which is completely free from fragments or threads of paste.

Equally valid results are obtained when using a silicone oil of 12,500 cst instead of 5000 cst.

In all cases, about 1.5 g of product per analysis are sufficient.

EXAMPLE 2

Binary composition with vinyl resin.

| | |
|---|---|
| silicone oil of 5000 cst density 0.97 g/cm$^3$ | 75 parts by weight |
| PVC ground to a particle size of $\leq 400\mu$ specific gravity 1.41 | 25 parts by weight |

After mixing in a mixer for some minutes, an almost translucent consistent paste is obtained of specific gravity 1.050 and possessing thixotropic properties, and which can be either preloaded into the sample tube or added at the time of analysis.

A quantity of between 1.2 and 1.5 grams is used, in all cases giving an excellent separation and filtration effect.

EXAMPLE 3

Binary composition with vinyl resin.

| | |
|---|---|
| silicone oil of 12,500 cst, density 0.97 g/cm$^3$ | 75 parts by weight |
| PVC ground to an average particle size of 1–5$\mu$ specific gravity 1.41, | 25 parts by weight |

| | |
|---|---|
| apparent density 0.33 g/ml | |

A fluid white paste having a specific gravity of 1.052 is obtained, and can be used with excellent results, especially if poured into the sample tube at the time of use.

If the silicone oil in said composition is replaced by an oil of 30,000 cst, a more consistent paste is obtained with a still better separation and filtration power. If however a silicone oil of 5000 cst is used, the results are decidedly unsatisfactory.

If the powdered PVC is replaced in the given composition by another having particles of average diameter 29$\mu$, apparent density 0.49 g/cm$^3$ and specific gravity 1.041, the effectiveness of the paste obtained is reduced decidedly.

The same happens if a PVC of average particle size 15$\mu$ is used.

EXAMPLE 4

Binary composition with fluorinated polymer.

| | |
|---|---|
| silicone oil of 30,000 cst density 0.97 g/cm$^3$ | 84 parts by weight |
| polyvinylidene fluoride of average particle size 0.250$\mu$ specific gravity 1.7, apparent density 0.2 g/cm$^3$ | 16 parts by weight |

After mixing, a translucent galatinous paste of specific gravity 1.042 is obtained, which gives excellent performance under all application conditions.

The greater cost of this composition due to the greater cost of the fluorinated polymer with respect to the polyethylene and PVC is compensated by the fact that it is so effective as to enable smaller quantities to be used than in the case of the preceding compositions.

0.9–1 are sufficient for a normal analysis sample tube, in comparison with the 1.2–1.5 grams of the compositions of the preceding examples.

A denser but equally effective paste is obtained by using a silicone oil of 60,000 cst in the same proportions.

EXAMPLE 5

Binary composition with vinyl polymer.

| | |
|---|---|
| silicone oil of 12,500 cst density 0.97 g/cm$^3$ | 80 parts by weight |
| powdered PVC with particle diameter 29$\mu$ specific gravity 1.41, apparent density 0.49 g/cm$^3$ | 17 parts by weight |
| micronised silica of apparent density 60 g/l | 3 parts by weight |

A white paste similar to cream is obtained with strong thixotropic properties and specific gravity 1.042, which gave good results under all conditions of application, except at the highest centrifuging speeds.

On using a PVC having a particle size firstly of 15$\mu$ and then of 1–5$\mu$, the results were increasingly less good.

EXAMPLE 6

Ternary composition with vinyl polymer.

| | |
|---|---|
| silicone oil of 30,000 cst | 80.5 parts by weight |

-continued

| | |
|---|---|
| density 0.97 g/cm³ | |
| powdered PVC of average particle size 29μ specific gravity 1.41, apparent density 0.49 g/cm³ | 16 parts by weight |
| micronised silica of apparent density 60 g/l | 3.5 parts by weight |

This paste was particularly effective at high centrifuging speeds.

Using the same ingredients a formulation having the following composition was attempted:

| | |
|---|---|
| silicone oil | 82 parts by weight |
| PVC | 13 parts by weight |
| micronised silica | 5 parts by weight | but the thixotropic properties were so bad as to make its application very limited.

EXAMPLE 7

Ternary composition with fluorinated polymer

| | |
|---|---|
| silicone oil of 5000 cst density 0.97 g/cm³ | 84 parts by weight |
| polyvinylidene fluoride of average particle size 0.250μ specific gravity 1.7, apparent density 0.2 g/cm³ | 15 parts by weight |
| micronised silica of apparent density 60 g/l | 1 part by weight |

A slightly gelatinous translucent paste of specific gravity 1.042 is obtained, which gives optimum results even when used in a quantity less than 1 gram.

EXAMPLE 8

Ternary composition comprising polyisobutylene

| | |
|---|---|
| silicone oil of 12,500 cst density 0.97 g/cm³ | 70 parts by weight |
| polyisobutylene of specific gravity 0.833 | 30 parts by weight |
| PVC of average particle size 1-5μ specific gravity 1.41, apparent density 0.33 g/cm³ | 50 parts by weight |

A white paste of medium consistency is obtained having a specific gravity of 1.044.

The efficiency is good under all experimental conditions, but not better than that obtained using only silicone oil.

However, in comparison to those compositions using only silicone oil, this type of formulation has the advantage of a decidedly lower cost.

EXAMPLE 9

Ternary composition with polyvinylidene fluoride

| | |
|---|---|
| silicone oil 5000 cst density 0.97 g/cm³ | 80.5 parts by weight |
| polyvinylidene fluoride of average particle size 0.250μ specific gravity 1.7, apparent density 0.2 g/cm³ | 14 parts by weight |
| micronised silica of apparent density 60 g/l | 5.5 parts by weight |

A highly gelatinous compact translucent composition is obtained of specific gravity 1.063.

When applied by a suitable spatula to the mouth of the sample tube, this composition creates a hermetic seal which during centrifuging becomes fluid and runs into the sample tube to form the separating baffle between the layer of erythrocytes and the serum.

Both the sealing of the sample tube and the filtration and separation functions were excellent.

EXAMPLE 10

Ternary composition with polyester resin

| | |
|---|---|
| silicone oil of 12,500 cst density 0.97 g/cm³ | 70 parts by weight |
| polycarbonate ground to a particle size of ≦250μ specific gravity 1.20 | 26.5 parts by weight |
| micronised silica of apparent density 60 g/l | 3.5 parts by weight |

An almost translucent consistent paste is obtained which behaves well in tests when using a quantity of about 1.3 g.

All the compositions of the preceding examples were subjected to rapid artificial ageing by placing them in an environment temperature-controlled at 58° C. for times of 2h, 24h and 48h.

No special difference was noted in the aged pastes except for a slight loss of thixotropic properties and a slight loss of coherence in those compositions comprising silicone oil of the lowest density and powdered polymer of the highest particle size.

Furthermore, all the compositions prepared and tried were found to be absolutely inert from the chemical and physiological aspects.

I claim:

1. Compositions which are able to separate the erythrocytes from the serum or plasma in a blood analysis sample by centrifuging, and having a specific gravity of between 1.010 and 1.100, characterised by comprising:
   a—a polydimethylsiloxane of viscosity between 5000 and 60,000 cst and density between 0.965 and 0.980 g/cm³
   b—a chemically and physically inert macromolecular substance of particle size between 0.200 and 450μ and specific gravity between 1.30 and 1.80, chosen from the group consisting of polyolefine resins, polyvinyl resins, fluorinated polyolefines and polyester resins.

2. Compositions as claimed in claim 1, characterised by also comprising:
   c—a fluid polyisobutylene of viscosity between 0.30 and 250 poises and density between 0.833 and 0.899 g/cm³
   d—amorphous micronised silica of particle size between 5 and 30 nm, apparent density between 30 and 80 g/l, and specific gravity 2.15.

3. Compositions as claimed in claims 1 or 2, wherein the components are present in the mixture in proportions within the following ranges:

| | |
|---|---|
| a - polydimethylsiloxane | 90-40 parts by weight |
| b - macromolecular substance | 10-34 parts by weight |
| c - polyisobutylene | 0-20 parts by weight |
| d - micronised silica | 0-6 parts by weight |

4. Compositions as claimed in claims 1 or 2, wherein the macromolecular substance is chosen from the group consisting of polyethylene, polyvinylchloride, polyvinylidene fluoride, and polyester.

5. A method for separating the erythrocytes from the serum or blood in blood analysis samples by centrifuging, characterised by using the compositions as claimed in claims 1 or 2 as the separator-filter medium.

* * * * *